(12) United States Patent
Hiraoka et al.

(10) Patent No.: US 8,617,606 B2
(45) Date of Patent: Dec. 31, 2013

(54) HYDROGEL SUSPENSION AND MANUFACTURING PROCESS THEREOF

(75) Inventors: Shogo Hiraoka, Tokushima (JP); Takakuni Matsuda, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 750 days.

(21) Appl. No.: 12/227,166

(22) PCT Filed: May 10, 2007

(86) PCT No.: PCT/JP2007/060087
§ 371 (c)(1), (2), (4) Date: Nov. 10, 2008

(87) PCT Pub. No.: WO2007/132907
PCT Pub. Date: Nov. 22, 2007

(65) Prior Publication Data
US 2009/0148529 A1 Jun. 11, 2009

(30) Foreign Application Priority Data

May 12, 2006 (JP) ................. 2006-133914

(51) Int. Cl.
*A61K 9/10* (2006.01)
*A61K 31/47* (2006.01)

(52) U.S. Cl.
USPC .......................... 424/486; 514/312

(58) Field of Classification Search
USPC ............... 424/486; 514/1, 312, 369, 789, 912
See application file for complete search history.

(56) References Cited

U.S. PATENT DOCUMENTS

| | | |
|---|---|---|
| 4,861,760 A | 8/1989 | Mazuel et al. |
| 5,366,985 A | 11/1994 | Nakayama et al. |
| 5,403,841 A | 4/1995 | Lang et al. |
| 5,624,962 A | 4/1997 | Takeuchi et al. |
| 6,060,486 A | 5/2000 | Urashima et al. |
| 2003/0152634 A1* | 8/2003 | Bodmeier .................. 424/489 |
| 2004/0063678 A1 | 4/2004 | Bellmann et al. |
| 2006/0039979 A1 | 2/2006 | Yamada et al. |
| 2006/0258703 A1 | 11/2006 | Shi et al. |
| 2007/0287729 A1 | 12/2007 | Matsuda et al. |

FOREIGN PATENT DOCUMENTS

| | | |
|---|---|---|
| EP | 1 568 359 A1 | 8/2005 |
| EP | 1 647 274 A1 | 4/2006 |
| JP | 5-186348 | 7/1993 |
| JP | 6-16556 | 1/1994 |
| JP | 06-016556 A * | 1/1994 |
| JP | 06-116137 | 4/1994 |
| JP | 6-67853 | 8/1994 |
| JP | 2729859 | 12/1997 |
| JP | 2001-518510 | 10/2001 |
| JP | 2003-095924 | 4/2003 |
| JP | 2005-206598 | 8/2005 |
| WO | WO 2006/028270 A1 | 3/2006 |
| WO | WO 2006/030851 A1 | 3/2006 |
| WO | WO 2006/052018 A1 | 5/2006 |
| WO | WO 2008/050896 A1 | 5/2008 |

OTHER PUBLICATIONS

Donshik et al, "Multicenter, Randomized, Double-Masked, Dose-Resonse, Placebo-Controlled, Parallel-Group Study of the Safety and Efficacy of Rebamipide (OPC-12759) Sterile Ophthalmic Suspension in the Treatment of Dry Eye". Invest Ophthalmol Vis Sci 2005;46:E-Abasract 2037.*

ShinEtsu, "Metolose: Water-Soluble Cellulose Ethers". ShinEtsu Chemical Co., dated 2005.*

* cited by examiner

*Primary Examiner* — Walter Webb
(74) *Attorney, Agent, or Firm* — Finnegan, Henderson, Farabow, Garrett & Dunner, L.L.P.

(57) ABSTRACT

The present invention relates to a hydrogel suspension which comprises a fine particle and high molecular weight hydroxypropylmethyl cellulose or methylcellulose, which exhibits high transparency and stability; and a manufacturing process thereof.

10 Claims, 2 Drawing Sheets

HYDROGEL SUSPENSION AND MANUFACTURING PROCESS THEREOF

TECHNICAL FIELD

The present invention relates to a hydrogel suspension which comprises a fine particle and high molecular weight hydroxypropylmethyl cellulose (hereinafter abbreviated to HPMC) or methylcellulose (hereinafter abbreviated to MC), which exhibits high transparency and stability; and a manufacturing process thereof. More specifically, the present invention relates to a hydrogel suspension which is obtainable by dissolving high molecular weight HPMC or MC powders in a suspension of a fine particle which may comprise an active ingredient of submicron-scale or nano-scale; or mixing the suspension of a fine particle together with a solution of high molecular weight HPMC or MC; and a manufacturing process thereof.

BACKGROUND ART

In case that a medicament is soluble in water or a solvent which is possible to be administered with the medicament, the medicament can be dissolved in the appropriate solvent to prepare a solution thereof and administered in the desired site or through an appropriate pathway to deliver the medicament to the site. On the contrary, in case that a medicament is poorly soluble in water or other appropriate solvent which is possible to be administered with the medicament, the solubility of the medicament for water or the appropriate solvent can be enhanced by, for example, milling the medicament to a fine particle state or making the crystalline state of the medicament a high energy state, and then a suspension or the other may be prepared with the resulting soluble medicament to be used for administration.

In order that the efficacy of a medicament is effectively exerted, it is necessary that the medicament is exposed to the desired site at the desired concentration for the desired period. However, it is thought that the retentivity of said conventional solution or suspension is low at the desired site and hence it is difficult to keep the desired period and concentration at the site. Then, in order to enhance the local retentivity of the medicament or make it sustained-released, a different drug formulation such as gel formulation and ointment may be often used. Especially, ophthalmic formulations have been studied about a variety of drug formulations such as a gel formulation and an ointment formulation so that the medicament would not easily flow through wink or lacrimal fluid (JP-A-2003-95924, JP-A-6-116137 (1994), JP-A-2005-206598, JP-A-2001-518510, JP-B-6-67853 (1994), JP-2729859).

The gelation technique known currently includes a method gelatinizing an aqueous pharmaceutical composition comprising Pluronic with heating, a method gelatinizing an aqueous pharmaceutical composition comprising carboxyvinyl polymer through pH change, a method gelatinizing an aqueous pharmaceutical composition comprising gellan gum or alginic acid by adding an ionic material, etc.

In order to prepare a gel formulation of a fine particle, it seems easy to prepare a suspension comprising the fine particle at first and add a gelatinizing agent thereto and then make it gelatinized. However, if a gelatinizing agent is added to a suspension of a fine particle, the energy balance at the surface of the fine particle will be lost to lead the energy to lower state, i.e. the energy is supposed to change to agglutinate the fine particle (i.e. to decrease the superficial area thereof). In addition, the fine particle can also be agglutinated by heating, changing pH, changing ionic concentration or adding a salt. If the fine particle is agglutinated, the improved solubility will be lowered. Thus, a conventional gelatinizing agent such as Pluronic with heating or an anionic gelatinizing agent such as carboxyvinyl polymer and gellan gum might have a problem about the fine particle-aggregation when used.

The transparency of a suspension wherein the particle size of the fine particle is not more than 100 nm will be enhanced, however, if a gelatinizing agent is added to the suspension and then the fine particle is agglutinated, the suspension might be turned to white. A gel formulation for ophthalmic use is useful because it makes the retentivity in the anterior eye segment improved. However, when the gel formulation is turned to white, the use thereof will be restricted because of a long-term blurred vision caused by the white turbidity. Anyhow, it was difficult to prepare a gel formulation which exhibits high transparency and stability, by easily gelatinizing a suspension of a fine particle by adding a gelatinizing agent thereto.

DISCLOSURE OF INVENTION

Problem to be Solved by the Invention

Therefore, it had been hoped to develop a gelatinizing agent for preparing a gel formulation comprising a fine particle gelatinized by adding the gelatinizing agent almost without agglutination, which exhibits high transparency and stability; the gel formulation; and a process for manufacturing the gel formulation.

Means to Solve the Problem

The present inventors have extensively studied to reach the above object and then have found that it is possible to prepare a hydrogel suspension as a gel formulation having an expected high transparency by adding high molecular weight HPMC or MC to a suspension of a fine particle which exhibit high transparency. Based upon the new findings, the present invention has been completed.

Namely, the present invention provides a hydrogel suspension which is obtainable by dissolving high molecular weight HPMC or MC powders in a suspension of a fine particle of submicron-scale or nano-scale; or mixing the suspension of a fine particle together with a solution of high molecular weight HPMC or MC; and a manufacturing process thereof. Furthermore, according to the manufacturing process, a suspension of a fine particle can be sterilized through sterile filtration, which also has an industrial merit to prepare such aseptic gel formulation without an aseptic active ingredient.

The invention provides various aspects as follows.

[1] A hydrogel suspension which comprises a suspension of a fine particle, and high molecular weight hydroxy-propylmethyl cellulose or methyl cellulose, and which exhibits high transparency and stability.

[2] The hydrogel suspension according to above [1], wherein the suspension of a fine particle comprises a fine particle and low molecular weight hydroxypropylmethyl cellulose.

[3] The hydrogel suspension according to above [1], wherein the suspension of a fine particle is an aqueous suspension which is obtainable by mixing at least one compound selected from water-soluble polymers and surfactants, an acidic or basic aqueous solution, and an aqueous solution containing a pharmaceutical compound.

[4] The hydrogel suspension according to above [3], wherein the acidic or basic aqueous solution is an acidic aqueous solution, and the pharmaceutical compound is a water-soluble salt of rebamipide.

[5] The hydrogel suspension according to above [3] or [4], wherein the at least one compound selected from water-soluble polymers and surfactants is low molecular weight hydroxypropylmethyl cellulose.

[6] The hydrogel suspension according to any one of above [3] to [5], wherein the aqueous suspension is acidic.

[7] The hydrogel suspension according to any one of above [1] to [6], which is obtainable by
adding a base to the aqueous suspension set forth in any one of above [3] to [6] to adjust pH thereof to 3 to 7,
dispersing and/or dialyzing it, then
adjusting pH thereof to 5 to 7, and adjusting the component concentration of the fine particle to 0.5 to 5% (w/v), and further
optionally sterilizing it by filtration.

[8] The hydrogel suspension according to any one of above [1] to [7], which is used for ophthalmic formulation, and which exhibits high transparency.

[9] A process for preparing a hydrogel suspension comprising
adding a base to the aqueous suspension set forth in any one of above [3] to [6] to adjust pH thereof to 3 to 7,
dispersing and/or dialyzing it, then
adjusting pH thereof to 5 to 7, and adjusting the component concentration of the fine particle to 0.5 to 5% (w/v), and
mixing the resulting suspension together with high molecular weight hydroxypropylmethyl cellulose or methyl cellulose.

[10] A process for preparing an aseptic hydrogel suspension comprising
adding a base to the aqueous suspension set forth in any one of above [3] to [6] to adjust pH thereof to 3 to 7,
dispersing and/or dialyzing it, then
adjusting pH thereof to 5 to 7, and adjusting the component concentration of the fine particle to 0.5 to 5% (w/v),
sterilizing it optionally by filtration, and
aseptically mixing the aseptic suspension obtained above together with an aseptic solution of high molecular weight hydroxypropylmethyl cellulose or methyl cellulose obtained optionally via filtration sterilization or autoclave sterilization.

[11] A re-gelable film which is obtainable by drying the hydrogel suspension set forth in any one of above [1] to [8].

EFFECT OF THE INVENTION

The gel prepared as mentioned above exhibits "thixotropy property", that is, a gel can change to a fluid sol when shaking and the sol can return to a gel again after standing for a certain period. Thus, on administering an oral drug, an intraoral drug, an ophthalmic formulation, an enteroclysis drug, etc. which each contains the gel, the gel can be fluidized so as to be put out of the container. After the administration, it is re-gelatinized and can be retained at the desired site for a long time.

The formulation comprising a hydrogel suspension of the invention can be selected in response to the purpose of therapy. It includes for example, an oral drug, an intraoral drug, an ophthalmic formulation, an enteroclysis drug and the like.

The most preferable embodiment of the invention is a gel formulation as an ophthalmic formulation comprising a hardly-soluble medicament, which exhibits high transparency. Especially, when the gel of the invention is applied to an aqueous suspension of crystalline rebamipide which has a high transparency, it has become possible to retain fine-particle rebamipide in the anterior eye segment and provide an ophthalmic gel formulation having a high transparency which is possible to prevent blurred vision. This formulation is thought to be very useful for treating dry eye, because the formulation can enhance the retentivity in the anterior eye segment, of rebamipide having an efficacy on treating dry eye, and retain the moisture in the anterior eye segment.

The gel formulation can be prepared as an aseptic formulation by mixing a suspension of a fine particle which is filtrated through a 0.2 µm filter together with a HPMC or MC solution which is sterilized through filter. Therefore, it has an industrial merit to simply prepare such aseptic formulation without an aseptic active ingredient.

In addition, it is possible to dry the formulation by air drying, lyophilizer and so on and then to return the dried formulation to a gel formulation by adding water thereto.

BEST MODE FOR CARRYING OUT THE INVENTION

Figure 1:
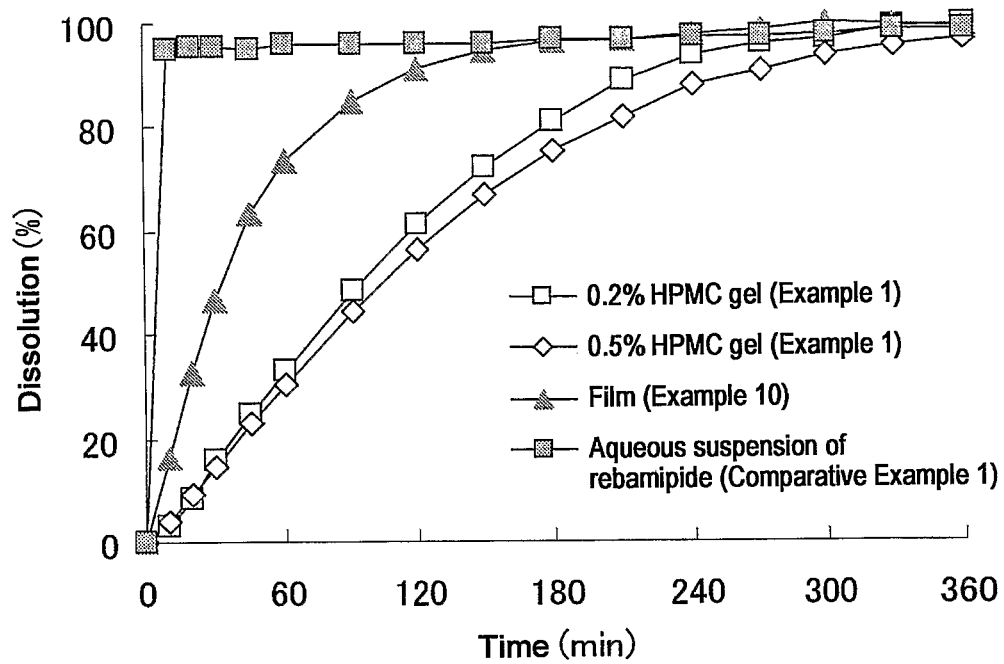
FIG. 1 shows dissolution behaviors of the gel formulations and the film formulation compared with the comparative example.

The ingredient in the present suspension of a fine particle can be an organic or inorganic material, preferably an organic material and more preferably a pharmaceutical compound. The examples of the ingredient include rebamipide [chemical name: 2-(4-chlorobenzoyl-amino)-3-[2(1H)-quinolon-4-yl] propionic acid] and a salt thereof. The salt of rebamipide described herein includes salts formed with a conventional base such as sodium hydroxide, potassium hydroxide, triethanolamine, trimethanol(tris[hydroxymethyl]aminomethane), meglumine, diethanolamine and the like, preferably a water-soluble salt such as the salt of sodium hydroxide. Rebamipide can be used as the above salt form or as a free acid, provided that it should be used with an equimolar or more of the above base when it is used as a free acid. The amount of the above-mentioned acid is preferably at least the amount required to neutralize the above base.

A process for preparing a fine particle from the above compound may be carried out with any of breakdown process such as a ball mill, a bead mill, a jet mill, and a hammer mill; spray dry; and built-up process such as crystallization.

The particle size of the fine particle which may be used in the invention is not more than 11=, preferably not more than 500 nm, and more preferably not more than 200 nm.

The more preferable suspension of a fine particle can be prepared by mixing at least one compound selected from water-soluble polymers and surfactants; an acidic or basic aqueous solution; and an aqueous solution containing a pharmaceutical compound. When the suspension of a fine particle is an aqueous suspension of crystalline rebamipide, the suspension may be prepared by mixing at least one compound selected from water-soluble polymers and surfactants; an acidic aqueous solution; and an aqueous solution containing a water-soluble salt of rebamipide; and crystallizing the rebamipide. Furthermore, an aqueous ophthalmic suspension of crystalline rebamipide can be prepared by adjusting the pH to 5-7 and arranging the concentration between 0.5 and 5% (w/v).

The above-mentioned crystalline rebamipide in the suspension can be crystallized as a fine particle form by (i) mixing an acidic aqueous solution containing at least one compound selected from water-soluble polymers and surfactants; and an aqueous solution containing a water-soluble salt of rebamipide;

(ii) mixing an acidic aqueous solution; and an aqueous solution containing a water-soluble salt of rebamipide and at least one compound selected from water-soluble polymers and surfactants; or (iii) mixing an acidic aqueous solution containing at least one compound selected from water-soluble polymers and surfactants; and an aqueous solution containing a water-soluble salt of rebamipide and at least one compound selected from water-soluble polymers and surfactants.

The water-soluble polymer and surfactant of the invention are used to obtain a certain surface property of the fine-particle ingredient and includes everything which can interact with a high molecular weight HPMC, for example, polyvinyl alcohol, hydroxypropylmethyl cellulose, hydroxyethyl cellulose, methylcellulose (MC), hydroxy-propylmethyl cellulose (HPMC), polyvinylpyrrolidone, polyethylene glycol (macrogol), polysorbate 80, sodium carboxymethylcellulose, carboxyvinyl polymer, water-soluble chitosan, sodium chondroitin sulfate, sodium alginate, hyaluronic acid, polyoxyethylene[160]polyoxypropylene[30]-glycol, polyoxyethylene[196]polyoxypropylene[67]glycol, polyoxyethylene hydrogenated castor oil 40, polyoxyethylene hydrogenated castor oil 60, polyoxyl 40 stearate and the like, preferably HPMC and MC, especially preferably low molecular weight HPMC. The viscosity grade of the low molecular weight HPMC (2% (w/v) aqueous solution) is preferably less than 50 mm$^2$/s, more preferably not more than 15 mm$^2$/s, even more preferably not more than 6 mm$^2$/s. In addition, it is possible that plural water-soluble polymers and surfactants exist as a mixture.

An acid used in the acidic aqueous solution can be a conventional acid such as hydrochloric acid, sulfuric acid, nitric acid, carbonic acid, phosphoric acid, citric acid and the like, preferably hydrochloric acid. In addition, a base used in the basic aqueous solution of the invention can include, for example, the same as the aforementioned conventional base.

The high molecular weight HPMC or MC used in the invention may be mixed as a solution together with the suspension of a fine particle, or may be directly dissolved as a powder in the suspension of a fine particle.

The methoxyl content and the hydroxypropoxyl content of the high molecular weight HPMC used in the invention are preferably 10-40% (w/w) and 1-20% (w/w), more preferably 19-30% (w/w) and 4-12% (w/w), even more preferably 27-30% (w/w) and 4-12% (w/w), respectively. The viscosity grade of the HPMC (2% (w/v) aqueous solution) is preferably not less than 15 mm$^2$/s, more preferably not less than 25 mm$^2$/s, even more preferably not less than 50 mm$^2$/s, especially preferably not less than 1500 mm$^2$/s.

The methoxyl content of the high molecular weight MC used in the invention is preferably 20-40% (w/w), more preferably 27-32% (w/w). The viscosity grade of the MC (2% (w/v) aqueous solution) is preferably not less than 15 mm$^2$/s, more preferably not less than 25 mm$^2$/s, even more preferably not less than 100 mm$^2$/s, especially preferably not less than 1500 mm$^2$/s.

The concentration of the high molecular weight HPMC or MC in the finally-prepared hydrogel suspension is preferably 0.001-10% (w/v), more preferably 0.01-5% (w/v), even more preferably 0.05-3% (w/v).

The concentration ratio between the fine-particle ingredient and the high molecular weight HPMC or MC is preferably 50:1-1:50, more preferably 20:1-1:1.

In the phrase "adding a base to the aqueous suspension to adjust pH thereof to 3 to 7, dispersing and/or dialyzing it, then adjusting pH thereof to 5 to 7, and adjusting the component concentration of the fine particle to 0.5 to 5%, and further sterilizing it optionally by filtration", the base used herein can include, for example, the same as the aforementioned conventional base.

The stirring and dispersing machines used herein are conventional stirring and dispersing machines used for pharmaceutical formulation such as a disperser, a homomixer, and a homogenizer, preferably a stirring and a dispersing machine which makes "agglomerated particles in the liquid" effectively-dispersed. The preferable examples include a rotary homogenizer such as ROBOMICS® (TOKUSHU KIKA KOGYO CO., LTD) and CLEARMIX®, as well as a wet-type jet mill and a high-pressure homogenizer. In particular, in using CLEARMIX® W-MOTION (M-TECHNIQUE CO., LTD.) wherein a screen and a rotor are counter-rotated at high speed to give a strong liquid-liquid shearing force, the transparency of the aqueous suspension containing crystalline rebamipide as prepared above can remarkably increase. Especially, an aqueous suspension of crystalline rebamipide mixed with hydroxypropylmethyl cellulose as an additive comprising water-soluble polymer exhibits a surprisingly high transparency.

The dialysis machines used herein include conventional dialysis machines used for pharmaceutical formulation such as Pellicon® (Nihon Millipore), Prostak® (Nihon Millipore), and Sartocon® (Sartorius). During the dialytic process, when the pH of an aqueous suspension containing crystalline rebamipide is low, the flow on dialytic membrane is low due to the agglomeration; while when the pH is high, rebamipide is dissolved and hereby the content thereof is decreased. Therefore, it is desirable that the dialysis procedure is carried out in the suspension at pH of 3-7, preferably pH of 4-7, more preferably pH of 5-7.

An aqueous suspension of crystalline rebamipide mixed with hydroxypropylmethyl cellulose as an additive comprising water-soluble polymer exhibits a surprisingly high transparency when desalted with a dialysis machine. Thereby, it has become possible to formulate a stable suspension whose aspect is unchanged under even high temperature.

The above dialyzing process and dispersing/stirring process may be carried out alone at each process or in combination; or the dispersing/stirring process may be carried out after the dialyzing process; or reversely the dialyzing process may be carried out after the dispersing/stirring process.

The suspension is concentrated through the dialyzing process, and hence the suspension of crystalline rebamipide at any concentration between 0.1% (w/v) and 10% (w/v), preferably between 0.5% (w/v) and 5% (w/v), can be prepared by diluting the concentrated suspension with purified water.

The term "re-gelation" in "re-gelable film" used herein means that when adding water to a film formed by drying the gel of the invention, the film can be re-formed into a gel exhibiting similar viscosity profile to the un-dried gel. The "drying (or dried)" described above can be carried out with air-drying, heat-drying, etc., but should not be construed to be limited thereto. In addition, the "film" refers to a thin membranous dry material which is prepared by drying the gel of the invention via the above-mentioned drying method(s) to remove the water in the gel. The film of the invention is a transparent film, which is characterized in that the gel reformed by adding water thereto exhibits similar viscosity profile to the un-dried gel, but it should not be construed to be limited thereto.

EXAMPLE

Hereinafter, the present invention is further illustrated by the following examples, but should not be construed to be limited thereto.

Example 1

366 mL of 10 N hydrochloric acid (432 g, 3.66 mol) and 7.8 L of 7.67% (w/v) aqueous solution of HPMC (grade: TC-5EW (viscosity of 2% (w/v) aqueous solution: 3 mm$^2$/s)) were mixed to prepare a solution of hydrochloric acid-HPMC (TC-5EW). To 21 L of aqueous sodium hydroxide which was prepared by adding purified water to 132 g of sodium hydroxide (3.3 mol), 600 g of rebamipide (1.62 mol) was added and dissolved with heating to give a sodium hydroxide-rebamipide solution.

The solution of hydrochloric acid-HPMC (TC-5EW) cooled at about 10° C. was allowed to circulate in a 350 mL vessel equipped with a disperser (CLEARMIX® S-MOTION, M-TECHNIQUE CO., LTD.) as an in-line type. The sodium hydroxide-rebamipide solution kept at 40-50° C. was injected by small and small to the 350 mL vessel with a CLEARMIX® S-MOTION wherein the rotor was turned at about 10,000 rpm to deposit a crystalline rebamipide. After completing the crystallization, the pH of the solution was about 1.5. To the crystal-deposited solution, 5 N sodium hydroxide was added to adjust the pH to about 5.90.

1 L of the resultant aqueous suspension containing rebamipide was dispersed for 20 minutes with a CLEARMIX® W-MOTION (M-TECHNIQUE CO., LTD.) wherein the rotor was turned at about 18,000 rpm and the screen was turned at about 16,000 rpm, and then the solution was concentrated and desalted with a dialysis machine (Millipore, Pellicon®2).

The sample given from the above concentrating/desalting process was diluted with purified water to prepare an aqueous suspension containing 2% (w/v) rebamipide.

The particle size of the prepared aqueous suspension containing rebamipide was about 100 nm by measuring with a Dynamic Light Scattering method (ZetasizerNano-ZS, Malvern).

In addition to the above suspension, each aqueous solution containing 0.1% (w/v), 0.4% (w/v), and 1.0% (w/v) HPMC (grade; 60SH4000 (the viscosity of 2% (w/v) aqueous solution: 4000 mm$^2$/s)) was also prepared.

Each of the aqueous suspension containing rebamipide and the aqueous solutions containing HPMC was filtrated for sterilization through 0.2 μm filter (Φ 47 mm, polyethylene-sulfone, PALL Co. Ltd.). After the above filtration, the aqueous suspension containing rebamipide and each kind of the three aqueous solutions containing HPMC were mixed in the ratio of 1:1 respectively. After the above mixing process, three kinds of gel were prepared, wherein the final concentrations of HPMC (60SH4000) were 0.05% (w/v), 0.2% (w/v), and 0.5% (w/v) and that of rebamipide was 1% (w/v), and which had various viscosities.

Example 2

According to the above Example 1, using HPMC (grade; TC-5EW (viscosity of 2% (w/v) aqueous solution: 3 mm$^2$/s)) as a water-soluble polymer, an aqueous suspension containing 2% (w/v) rebamipide was prepared. The particle size of the prepared aqueous suspension containing rebamipide was about 100 nm by measuring with a Dynamic Light Scattering method (ZetasizerNano-ZS, Malvern).

In addition to the above suspension, each aqueous solution containing 0.1% (w/v), 0.4% (w/v), and 1.0% (w/v) HPMC (grade; 60SH10000 (the viscosity of 2% (w/v) aqueous solution: 10000 mm$^2$/s)) was also prepared.

The aqueous suspension containing rebamipide and each kind of the three aqueous solutions containing HPMC were mixed in the ratio of 1:1 respectively. After the above mixing process, three kinds of gel were prepared, wherein the final concentrations of HPMC (60SH10000) were 0.05% (w/v), 0.2% (w/v), and 0.5% (w/v) and that of rebamipide was 1%, and which had various viscosities.

Example 3

According to the above Example 1, using HPMC (grade; TC-5EW (viscosity of 2% (w/v) aqueous solution: 3 mm$^2$/s)) as a water-soluble polymer, an aqueous suspension containing 2% (w/v) rebamipide was prepared. The particle size of the prepared aqueous suspension containing rebamipide was about 100 nm by measuring with a Dynamic Light Scattering method (ZetasizerNano-ZS, Malvern).

In addition to the above suspension, each aqueous solution containing 0.1% (w/v), 0.4% (w/v), and 1.0% (w/v) HPMC (grade; 60SH50 (the viscosity of 2% (w/v) aqueous solution: 50 mm$^2$/s)) was also prepared.

Each of the aqueous suspension containing rebamipide and the aqueous solution containing HPMC was filtrated for sterilization through 0.2 μm filter (Φ 47 mm, polyethylene-sulfone, PALL Co. Ltd.). After the above filtration, the aqueous suspension containing rebamipide and each kind of the three aqueous solutions containing HPMC were mixed in the ratio of 1:1 respectively. After the above mixing process, three kinds of gel were prepared, wherein the final concentrations of HPMC (60SH50) were 0.05% (w/v), 0.2% (w/v), and 0.5% (w/v) and that of rebamipide was 1% (w/v), and which had various viscosities.

Example 4

366 mL of 10 N hydrochloric acid (432 g, 3.66 mol) and 7.8 L of 7.67% (w/v) aqueous solution of HPMC (grade: TC-5EW (viscosity of 2% (w/v) aqueous solution: 3 mm$^2$/s)) were mixed to prepare a solution of hydrochloric acid-HPMC (TC-5EW). To 21 L of aqueous sodium hydroxide which was prepared by adding purified water to 132 g of sodium hydroxide (3.3 mol), 600 g of rebamipide (1.62 mol) was added and dissolved with heating to give a sodium hydroxide-rebamipide solution.

The solution of hydrochloric acid-HPMC (TC-5EW) cooled at about 10° C. was allowed to circulate in a 350 mL vessel equipped with a disperser (CLEARMIX® S-MOTION, M-TECHNIQUE CO., LTD.) as an in-line type. The sodium hydroxide-rebamipide solution kept at 40-50° C. was injected by small and small to the 350 mL vessel with a CLEARMIX® S-MOTION wherein the rotor was turned at about 10,000 rpm to deposit a crystalline rebamipide. After completing the crystallization, the pH of the solution was about 1.5. To the crystal-deposited solution, 5 N sodium hydroxide was added to adjust the pH to about 5.90.

1 L of the resultant aqueous suspension containing rebamipide was dispersed for 20 minutes with a CLEARMIX® W-MOTION (M-TECHNIQUE CO., LTD.) wherein the rotor was turned at about 18,000 rpm and the screen was turned at about 16,000 rpm, and then the solution was concentrated and desalted with a dialysis machine (Millipore, Pellicon®2).

The sample given from the above concentrating/desalting process was diluted with purified water to prepare an aqueous suspension containing 4% (w/v) rebamipide.

The particle size of the prepared aqueous suspension containing rebamipide was about 100 nm by measuring with a Dynamic Light Scattering method (ZetasizerNano-ZS, Malvern).

In addition to the above suspension, each aqueous solution containing 0.1% (w/v), 0.4% (w/v), and 1.0% (w/v) HPMC (grade; 60SH4000 (the viscosity of 2% (w/v) aqueous solution: 4000 mm$^2$/s)) was also prepared.

Each of the aqueous suspension containing rebamipide and the aqueous solutions containing HPMC was filtrated for sterilization through 0.2 μm filter (Φ47 mm, polyethylenesulfone, PALL Co. Ltd.). After the above filtration, the aqueous suspension containing rebamipide and each kind of the three aqueous solutions containing HPMC were mixed in the ratio of 1:1 respectively. After the above mixing process, three kinds of gel were prepared, wherein the final concentrations of HPMC (60SH4000) were 0.05% (w/v), 0.2% (w/v), and 0.5% (w/v) and that of rebamipide was 2% (w/v), and which had various viscosities.

Example 5

According to the above Example 4, using HPMC (grade; TC-5EW (viscosity of 2% (w/v) aqueous solution: 3 mm$^2$/s)) as a water-soluble polymer, an aqueous suspension containing 4% (w/v) rebamipide was prepared. The particle size of the prepared aqueous suspension containing rebamipide was about 100 nm by measuring with a Dynamic Light Scattering method (ZetasizerNano-ZS, Malvern).

In addition to the above suspension, each aqueous solution containing 0.1% (w/v), 0.4% (w/v), and 1.0% (w/v) HPMC (grade; 60SH50 (the viscosity of 2% (w/v) aqueous solution: 50 mm$^2$/s)) was also prepared.

Each of the aqueous suspension containing rebamipide and the aqueous solution containing HPMC was filtrated for sterilization through 0.2 μm filter (φ 47 mm, polyethylenesulfone, PALL Co. Ltd.). After the above filtration, the aqueous suspension containing rebamipide and each kind of the three aqueous solutions containing HPMC were mixed in the ratio of 1:1 respectively. After the above mixing process, three kinds of gel were prepared, wherein the final concentrations of HPMC (60SH50) were 0.05% (w/v), 0.2% (w/v), and 0.5% (w/v) and that of rebamipide was 2% (w/v), and which had various viscosities.

Example 6

According to the above Example 1, using HPMC (grade; TC-5EW (viscosity of 2% (w/v) aqueous solution: 3 mm$^2$/s)) as a water-soluble polymer, an aqueous suspension containing 2% (w/v) rebamipide was prepared. The particle size of the prepared aqueous suspension containing rebamipide was about 100 nm by measuring with a Dynamic Light Scattering method (ZetasizerNano-ZS, Malvern).

In addition to the above suspension, each aqueous solution containing 0.1% (w/v), 0.4% (w/v), and 1.0% (w/v) HPMC (grade; 60SH4000 (the viscosity of 2% (w/v) aqueous solution: 4000 mm$^2$/s)) was also prepared. In each solution, glycerin was dissolved wherein the concentration of the glycerin was 4.7% (w/v).

Each of the aqueous suspension containing rebamipide and the aqueous solution containing HPMC was filtrated for sterilization through 0.2 μm filter (Φ 47 mm, polyethylenesulfone, PALL Co. Ltd.). After the above filtration, the aqueous suspension containing rebamipide and each kind of the three aqueous solutions containing HPMC were mixed in the ratio of 1:1 respectively. After the above mixing process, three kinds of gel were prepared, wherein the final concentrations of HPMC (60SH4000) were 0.05% (w/v), 0.2% (w/v), and 0.5% (w/v) and that of rebamipide was 1% (w/v), and which had various viscosities.

Example 7

According to the above Example 1, using HPMC (grade; TC-5EW (viscosity of 2% (w/v) aqueous solution: 3 mm$^2$/s)) as a water-soluble polymer, an aqueous suspension containing 2% (w/v) rebamipide was prepared. The particle size of the prepared aqueous suspension containing rebamipide was about 100 nm by measuring with a Dynamic Light Scattering method (ZetasizerNano-ZS, Malvern).

In addition to the above suspension, an aqueous solution containing 1.0% (w/v) MC (grade; SM400 (the viscosity of 2% (w/v) aqueous solution: 400 mm$^2$/s)) was also prepared.

Each of the aqueous suspension containing rebamipide and the aqueous solution containing MC was filtrated for sterilization through 0.2 μm filter (Φ 47 mm, polyethylenesulfone, PALL Co. Ltd.). After the above filtration, the aqueous suspension containing rebamipide and the aqueous solutions containing MC were mixed in the ratio of 1:1. After the above mixing process, gel was prepared, wherein the final concentration of MC was 0.5% (w/v) and that of rebamipide was 1% (w/v).

Example 8

According to the above Example 1, using HPMC (grade; TC-5EW (viscosity of 2% (w/v) aqueous solution: 3 mm$^2$/s)) as a water-soluble polymer, an aqueous suspension containing 2% (w/v) rebamipide was prepared. The particle size of the prepared aqueous suspension containing rebamipide was about 100 nm by measuring with a Dynamic Light Scattering method (ZetasizerNano-ZS, Malvern).

In addition to the above suspension, an aqueous solution containing 0.4% (w/v) MC (grade; SM1500 (the viscosity of 2% (w/v) aqueous solution: 1500 mm$^2$/s)) was also prepared.

Each of the aqueous suspension containing rebamipide and the aqueous solution containing MC was filtrated for sterilization through 0.2 μm filter (Φ 47 mm, polyethylenesulfone, PALL Co. Ltd.). After the above filtration, the aqueous suspension containing rebamipide and the aqueous solutions containing MC were mixed in the ratio of 1:1. After the above mixing process, gel was prepared, wherein the final concentration of MC was 0.2% and that of rebamipide was 1%.

Example 9

The gel containing 0.2% (w/v) HPMC (60SH4000) and the gel containing 0.5% (w/v) HPMC (60SH4000) which were prepared in Example 1 were lyophilized to give lyophilized hydrogel suspension.

Example 10

The gel containing 0.2% (w/v) HPMC (60SH4000) and the gel containing 0.5% (w/v) HPMC (60SH4000) which were prepared in Example 1 were air-dried on a vinyl sheet to give dried hydrogel suspension. The dried one was a film-like material having an extremely high transparency.

Comparative Example 1

Aqueous suspension containing 2% (w/v) rebamipide prepared in Example 1 and purified water were mixed in 1:1 to give aqueous suspension containing 1% (w/v) rebamipide.

Experiment 1

To the dried materials of above Example 9 and Example 10, water was added to provide the material re-gelatinized.

Experiment 2

The gel containing 0.2% (w/v) HPMC (60SH4000) and the gel containing 0.5% (w/v) HPMC (60SH4000) which were prepared in above Example 1; the air-dried film formulation containing 0.2% (w/v) HPMC (60SH4000) which was prepared in above Example 10; and aqueous suspension containing 1% (w/v) rebamipide which was prepared in above Comparative Example 1 were tested via the dissolution test of the Japanese Pharmacopoeia using Method 2 (paddle method) [resolution medium: 900 mL of disodium hydrogen phosphate•citrate buffer (pH 6); rotational speed: 50 rpm]. The gel material was filled in capsules and then thrown into the test vessels. The air-dried film formulation and the aqueous suspension containing 1% (w/v) rebamipide were directly thrown into the test vessels without anything to formulate them.

The dissolution behaviors of the gel formulations and the air-dried film formulation exhibited more sustained release than that of the aqueous suspension (FIG. 1).

Experiment 3

Figure 2:
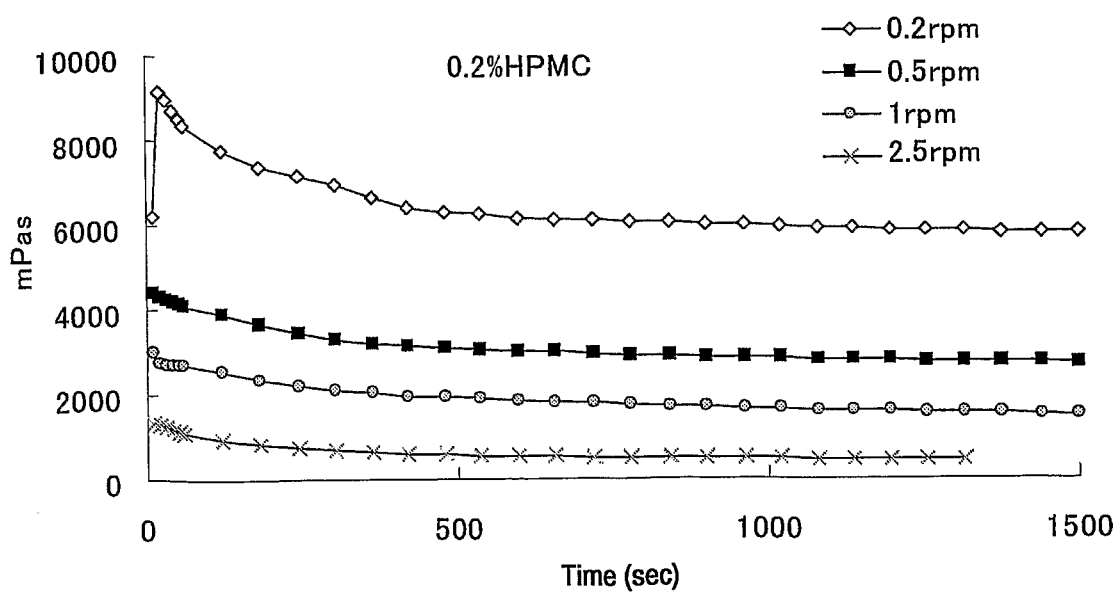
FIG. 2 shows the correlation between the loading time of a shear stress on the gel (0.2% HPMC) and the viscosity thereof (rotational speed of the rotational viscometer: 0.2-2.5 rpm).
Figure 3:
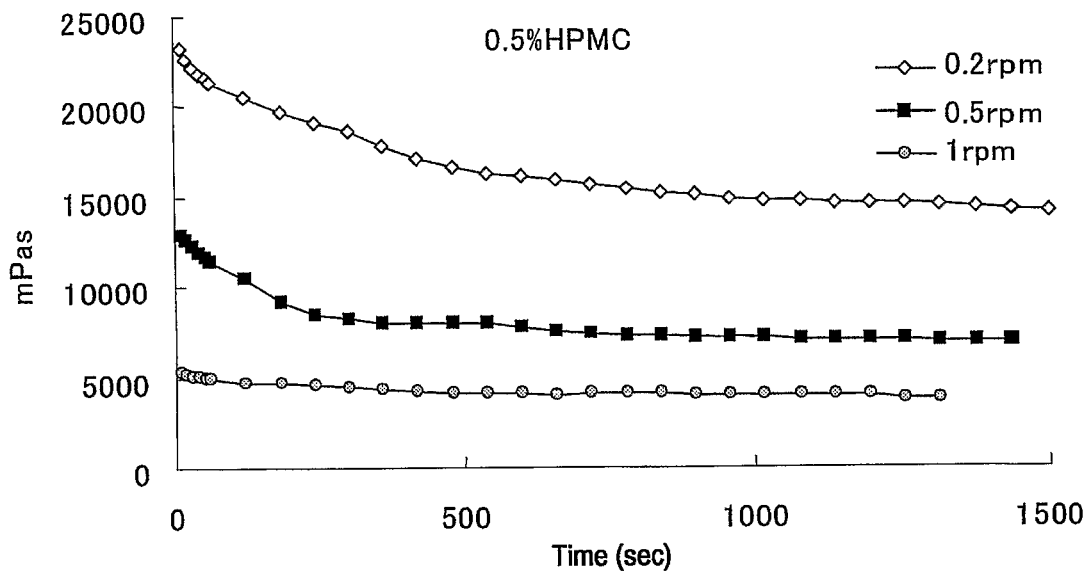
FIG. 3 shows the correlation between the loading time of a shear stress on the gel (0.5% HPMC) and the viscosity thereof (rotational speed of the rotational viscometer: 0.2-1.0 rpm).
Figure 4:
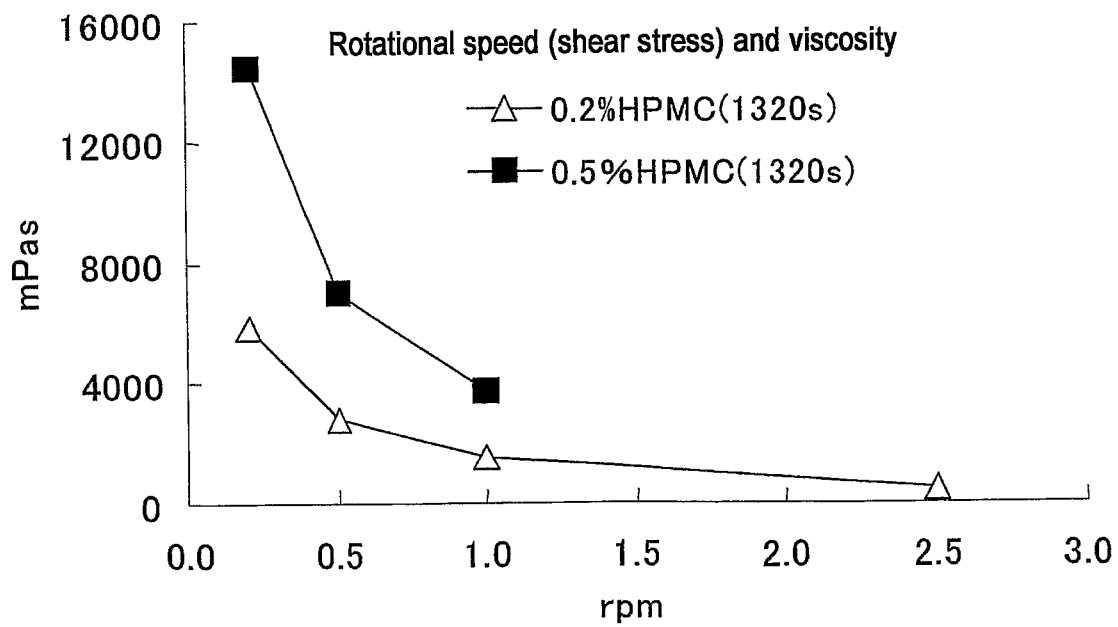
FIG. 4 shows the evaluation of the thixotropy property of each gel (the correlation between the shear stress (rotational speed) and the viscosity thereof, at 1,320 seconds).

The gel containing 0.2% (w/v) HPMC (60SH4000) and the gel containing 0.5% (w/v) HPMC (60SH4000) which were prepared in above Example 1 were loaded with various shear stress using a rotational viscometer, and the viscosity change thereof was recorded under the time course of the loading (FIG. 2-FIG. 4). On both of the gels, the stronger shear stress induced to lower viscosity thereof more, and the longer loading time of the stress also induced to do it more. This is caused by the thixotropy property of the gels.

Experiment 4

The viscosity of the gels which were prepared in above Examples 1 to 5 was measured using a rotational viscometer (rotational speed: 100 rpm) and then it has been found that the viscosity of the gels could be changed according to the grade and the concentration of the high molecular weight HPMC (Table 1). Therefore, it has been found that the viscosity can be adjusted by changing the factors of the HPMC. The concentration of the fine particle also influenced the viscosity.

TABLE 1

The viscosity of the gels prepared with various concentrations of HPMC (Measured at 37° C., at 100 rpm; Unit: mPa · s)

| 1% (w/v) Rebamipide | | | | | | | | |
|---|---|---|---|---|---|---|---|---|
| 60SH50 | | | 60SH4000 | | | 60SH10000 | | |
| 0.05% | 0.2% | 0.5% | 0.05% | 0.2% | 0.5% | 0.05% | 0.2% | 0.5% |
| 2.0 | 2.6 | 2.8 | 2.9 | 14.4 | 14.7 | 5.9 | 30.0 | 40.9 |

| 2% (w/v) Rebamipide | | | | | |
|---|---|---|---|---|---|
| 60SH50 | | | 60SH4000 | | |
| 0.05% | 0.2% | 0.5% | 0.05% | 0.2% | 0.5% |
| 5.4 | 6.3 | 12.3 | 6.1 | 8.5 | 20.1 |

INDUSTRIAL APPLICABILITY

According to the process of the invention, a hydrogel suspension which exhibits high transparency and stability can be prepared via such a simple process, and hence the utility of the process will be expected in the field of various drug formulations, especially ophthalmic formulation. Especially, when applying the present invention to the aqueous suspension of crystalline rebamipide which exhibits high transparency, it will be possible to retain fine-particle rebamipide in the anterior eye segment and additionally to provide an ophthalmic gel formulation having a high transparency which is possible to prevent blurred vision. This formulation is expected to be useful for treating dry eye, from the viewpoint that the formulation can enhance the retentivity in the anterior eye segment, of rebamipide having an efficacy on treating dry eye, and retain the moisture in the anterior eye segment.

In addition, according to the invention, the gel formulation can be prepared as a sterile formulation by mixing a suspension of a fine particle and HPMC or MC solution after each of the components is sterilized through filter. Therefore, the sterile gel formulation can be prepared by such a simplified process without an aseptic active ingredient.

The invention claimed is:

1. A hydrogel suspension which comprises
   (1) an aqueous suspension of fine particles which comprises (i) at least one compound selected from water-soluble polymers and surfactants, (ii) an acidic aqueous solution, and (iii) an aqueous solution containing a water-soluble salt of rebamipide; the particle size of which is not more than 500 nm; and which is obtainable by (i) mixing an acidic aqueous solution containing at least one compound selected from water-soluble polymers and surfactants, and an aqueous solution containing a water-soluble salt of rebamipide, (ii) mixing an acidic aqueous solution, and an aqueous solution containing a water-soluble salt of rebamipide and at least one compound selected from water-soluble polymers and surfactants, or (iii) mixing an acidic aqueous solution containing at least one compound selected from water-soluble polymers and surfactants, and an aqueous solution containing a water-soluble salt of rebamipide and at least one compound selected from water-soluble polymers and surfactants, and
   (2) (i) hydroxypropylmethyl cellulose whose methoxyl content and hydroxypropoxyl content are 10-40% (w/w) and 1-20% (w/w), respectively, and whose viscosity grade (2% (w/v) aqueous solution) is not less than 1500 mm$^2$/s; or (ii) methyl cellulose whose methoxyl content is 20-40% (w/w), and whose viscosity grade (2% (w/v) aqueous solution) is not less than 1500 mm$^2$/s.

2. The hydrogel suspension according to claim 1, wherein the ingredient of (2) is hydroxypropylmethyl cellulose whose methoxyl content and hydroxypropoxyl content are 10-40 (w/w) and 1-20% (w/w), respectively, and whose viscosity grade (2% (w/v) aqueous solution) is not less than 1500 mm$^2$/s.

3. The hydrogel suspension according to claim 1, wherein the methoxyl content and the hydroxypropoxyl content of the hydroxypropylmethyl cellulose in (2) are 19-30 (w/w) and 4-12% (w/w), respectively, and the viscosity grade (2% (w/v) aqueous solution) thereof is not less than 1500 mm$^2$/s.

4. The hydrogel suspension according to claim 1, wherein the at least one compound selected from water-soluble polymers and surfactants in (1) is hydroxypropylmethyl cellulose whose viscosity grade (2% (w/v) aqueous solution) is not more than 15 mm$^2$/s.

5. The hydrogel suspension according to claim 1, wherein the aqueous suspension is acidic.

6. The hydrogel suspension according to any one of claim 1 to 3, 4 or 5, which is obtainable by
adding a base to the aqueous suspension set forth in any one of claim 1 to 3, 4 or 5 to adjust pH thereof to 3 to 7,
dispersing and/or dialyzing it, then
adjusting pH thereof to 5 to 7, and adjusting the component concentration of the fine particle to 0.5 to 5% (w/v), further
optionally sterilizing it by filtration, and
mixing the resulting suspension together with the hydroxypropylmethyl cellulose or methyl cellulose of (2).

7. The hydrogel suspension according to claim 6, which is used for ophthalmic formulation.

8. A process for preparing a hydrogel suspension comprising
adding a base to the aqueous suspension set forth in any one of claim 1 to 3, 4 or 5 to adjust pH thereof to 3 to 7,
dispersing and/or dialyzing it, then
adjusting pH thereof to 5 to 7, and adjusting the component concentration of the fine particle to 0.5 to 5% (w/v), and
mixing the resulting suspension together with the hydroxypropylmethyl cellulose or methyl cellulose set forth in any one of claim 1 to 3, 4 or 5.

9. A process for preparing an aseptic hydrogel suspension comprising
adding a base to the aqueous suspension set forth in any one of claim 1 to 3, 4 or 5 to adjust pH thereof to 3 to 7,
dispersing and/or dialyzing it, then
adjusting pH thereof to 5 to 7, and adjusting the component concentration of the fine particle to 0.5 to 5% (w/v),
sterilizing it optionally by filtration, and
aseptically mixing the aseptic suspension obtained above together with an aseptic solution of the hydroxypropylmethyl cellulose or methyl cellulose set forth in any one of claims 1 to 3, 4 or 5 which is obtained optionally via filtration sterilization or autoclave sterilization.

10. A re-getable film which is obtainable by drying the hydrogel suspension set forth in claim 6.

* * * * *

UNITED STATES PATENT AND TRADEMARK OFFICE
CERTIFICATE OF CORRECTION

| | | |
|---|---|---|
| PATENT NO. | : 8,617,606 B2 | Page 1 of 1 |
| APPLICATION NO. | : 12/227166 | |
| DATED | : December 31, 2013 | |
| INVENTOR(S) | : Hiraoka et al. | |

It is certified that error appears in the above-identified patent and that said Letters Patent is hereby corrected as shown below:

In The Claims

Claim 6, col. 13, lines 23-24, "any one of claim 1 to 3, 4, or 5" should read -- any one of claims 1 to 3, 4, or 5 --.

Claim 6, col. 13, lines 25-26, "any one of claim 1 to 3, 4, or 5" should read -- any one of claims 1 to 3, 4, or 5 --.

Claim 8, col. 14, lines 7-8, "any one of claim 1 to 3, 4, or 5" should read -- any one of claims 1 to 3, 4, or 5 --.

Claim 8, col. 14, line 14, "any one of claim 1 to 3, 4, or 5" should read -- any one of claims 1 to 3, 4, or 5 --.

Claim 9, col. 14, lines 18-19, "any one of claim 1 to 3, 4, or 5" should read -- any one of claims 1 to 3, 4, or 5 --.

Signed and Sealed this
Twenty-fourth Day of March, 2015

Michelle K. Lee
*Director of the United States Patent and Trademark Office*